(12) United States Patent
Yang (10) Patent No.: US 10,272,001 B2
(45) Date of Patent: Apr. 30, 2019

(54) ABSORBENT ARTICLE INCLUDING RESILIENT ABSORBENT COMPOSITE MATERIAL

(75) Inventor: Morris Yang, Princeton Junction, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 1430 days.

(21) Appl. No.: 13/236,784

(22) Filed: Sep. 20, 2011

(65) Prior Publication Data

US 2013/0072890 A1    Mar. 21, 2013

(51) Int. Cl.
*A61F 13/15* (2006.01)
*A61F 13/534* (2006.01)
*A61F 13/537* (2006.01)

(52) U.S. Cl.
CPC ...... *A61F 13/534* (2013.01); *A61F 13/53704* (2013.01); *A61F 13/53752* (2013.01)

(58) Field of Classification Search
CPC .............. A61F 13/534; A61F 13/53704; A61F 13/53752
USPC ................................. 604/358, 367, 369, 370
See application file for complete search history.

(56) References Cited

U.S. PATENT DOCUMENTS

| | | | |
|---|---|---|---|
| 4,589,876 A | 5/1986 | Van Tilburg | |
| 4,608,047 A | 8/1986 | Mattingly | |
| 4,687,478 A | 8/1987 | Van Tilburg | |
| 4,806,408 A * | 2/1989 | Pierre et al. | 428/76 |
| 4,900,320 A | 2/1990 | McCoy | |
| 5,821,179 A * | 10/1998 | Masaki et al. | 442/375 |
| 6,403,857 B1 | 6/2002 | Gross et al. | |
| 6,458,877 B1 * | 10/2002 | Ahmed et al. | 524/275 |
| 6,479,415 B1 | 11/2002 | Erspamer et al. | |
| 6,790,798 B1 | 9/2004 | Suzuki et al. | |
| 7,462,755 B2 * | 12/2008 | Toro et al. | 604/378 |
| 7,842,386 B2 | 11/2010 | Loeker et al. | |
| 8,148,598 B2 | 4/2012 | Tsang et al. | |
| 2003/0003830 A1 * | 1/2003 | Ouederni et al. | 442/327 |
| 2003/0236512 A1 * | 12/2003 | Baker | 604/385.01 |
| 2005/0148258 A1 * | 7/2005 | Chakravarty et al. | 442/327 |
| 2006/0009743 A1 | 1/2006 | Wang et al. | |
| 2006/0058751 A1 * | 3/2006 | Rosenfeld et al. | 604/380 |
| 2006/0058754 A1 | 3/2006 | Rosenfeld et al. | |
| 2006/0142714 A1 * | 6/2006 | Jackson et al. | 604/364 |
| 2006/0184149 A1 | 8/2006 | Kasai et al. | |
| 2007/0197987 A1 * | 8/2007 | Tsang et al. | 604/365 |
| 2008/0071237 A1 | 3/2008 | Chen et al. | |
| 2008/0262455 A1 | 10/2008 | Soerens et al. | |

FOREIGN PATENT DOCUMENTS

| | | | | |
|---|---|---|---|---|
| EP | 1013291 A1 * | 6/2000 | | A61L 15/58 |
| EP | 1319414 A1 | 6/2003 | | |
| WO | WO 2001/026593 A1 | 4/2001 | | |

OTHER PUBLICATIONS

Brodof, Superabsorbent, Continuous Filament Web, Jul. 2, 1996, USSIR H1565, pp. 1-7.*

* cited by examiner

*Primary Examiner* — Bradley H Philips (57) ABSTRACT

The present invention relates to an absorbent composite material and a absorbent article including such absorbent composite material. More particularly, the present invention relates to an absorbent composite material for use in sanitary absorbent products such as sanitary napkins, pantiliners, diapers, adult incontinence products, and the like.

20 Claims, 10 Drawing Sheets

ABSORBENT ARTICLE INCLUDING RESILIENT ABSORBENT COMPOSITE MATERIAL

FIELD OF INVENTION

The present invention generally relates to an absorbent composite material and an absorbent article including such absorbent composite material. More particularly, the present invention relates to an absorbent composite material for use in sanitary absorbent articles such as sanitary napkins, pantiliners, diapers, adult incontinence products, and the like.

BACKGROUND OF THE INVENTION

Lofty, resilient, non-woven webs, that is nonwoven webs that have a high degree of loft and the tendency to retain such loft in both the dry and wet state, are well known. In addition, it is well known that such lofty, resilient, nonwoven webs may be used in disposable sanitary products such as sanitary napkins, pantiliners, tampons, diapers, adult incontinence products, and the like. A perceived benefit of such lofty, resilient, nonwoven webs is that such materials may deliver enhanced comfort to a user of such disposable sanitary products since the lofty, resilient, nonwoven webs may tend to conform to, and move with, the user's body during use.

A problem with lofty, resilient, nonwoven webs is that due to the loft of such materials (i.e. their low density) such webs are not particularly absorbent. In addition, such materials may exhibit poor rewet properties. That is, such materials may release or "wet back" fluid when subjected to an external pressure.

In view of the foregoing there is a need for an absorbent composite material that includes an exceptionally resilient, soft, cushiony nonwoven web and simultaneously provides superior fluid handling characteristics.

SUMMARY OF THE INVENTION

In view of the foregoing, the present invention provides an absorbent article including a liquid permeable cover layer, a liquid impermeable barrier layer, and an absorbent composite material arranged between the cover layer and the barrier layer, wherein the absorbent composite material includes a fibrous material including a plurality of individual fibers forming a fiber matrix and a binder material present in an amount from about 20% by to about 60% by weight of the fibrous material, the fibrous material having first and second opposed surfaces, superabsorbent polymer dispersed within the fiber matrix, and an absorbent mixture arranged adjacent to the first surface of the fibrous material, the absorbent mixture including superabsorbent polymer and adhesive.

BRIEF DESCRIPTION OF THE DRAWINGS

Examples of embodiments of the present invention will now be described with reference to the drawings, in which.

DETAILED DESCRIPTION OF THE INVENTION

The present invention generally relates to an absorbent composite material for use in disposable absorbent articles such as sanitary napkins, pantiliners, absorbent products for incontinence, and other disposable sanitary absorbent articles worn close to a wearer's body. Although the absorbent composite material according to the present invention will be described herein with reference to a sanitary napkin, the absorbent composite material may be utilized in other disposable sanitary absorbent articles.

The absorbent composite material according to the present invention, as described in detail below, is structured and arranged such that it provides superior fluid absorbing properties and at the same time is "resilient". The term "resilient" as used herein means that the absorbent composite material tends to retain its shape both in the dry and wet states and when subjected to a compression force tends to recover its original shape when such force is removed. Absorbent articles according to the present invention including the inventive absorbent composite material are thin, flexible, resilient in the x, y and z directions, and exhibit superior fluid handling characteristics. "Resilient in the x, y and z direction" as used herein means the absorbent article exhibits resiliency properties in the transverse direction of the article, in the longitudinal direction of the article, and the direction extending into the article.

Figure 1:
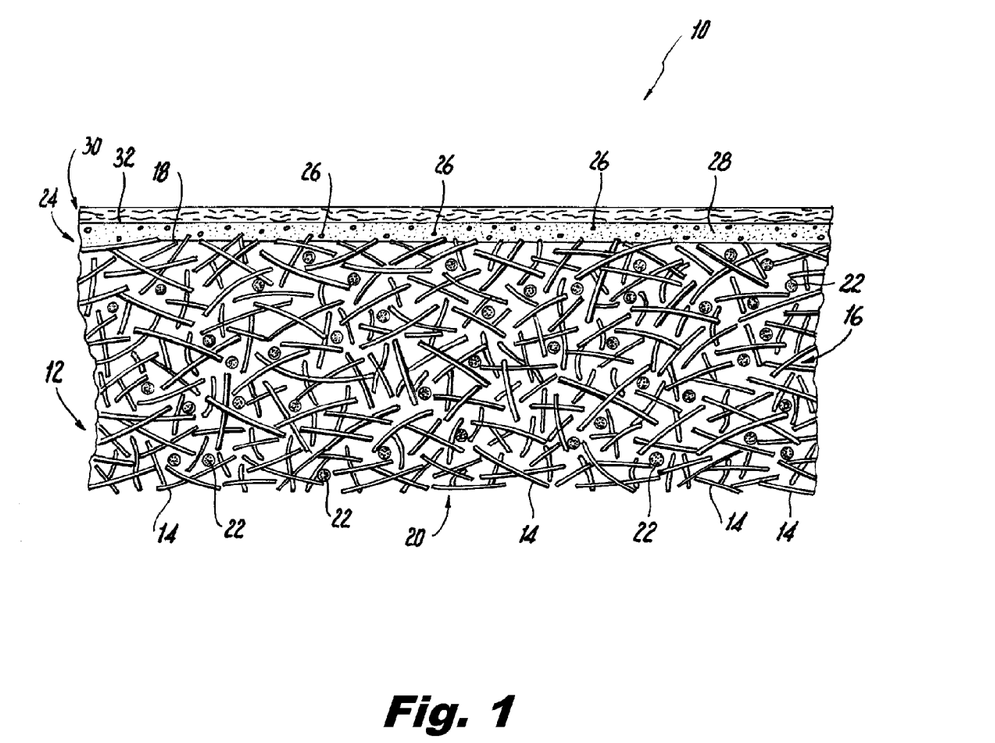
FIG. 1 is a sectional schematic view of an absorbent composite material according to a first embodiment of the present invention.

Reference is made to FIG. 1 which illustrates a sectional view of an absorbent composite material 10 according to a first embodiment of the present invention. As shown, the absorbent composite material 10 includes, in part, a fibrous material 12 including a plurality of individual fibers 14 that form a fiber matrix 16. The fibrous material 12 generally includes a top (or first) surface 18 and an opposed bottom (or second) surface 20.

The fibrous material 12 is preferably a fibrous nonwoven material made by a known nonwoven manufacturing technique such as an airlaid process, a card and bind process or a resin and adhesive bond process. Preferably the nonwoven material is a "high loft" nonwoven. Specifically, the nonwoven preferably has a density lower than 0.05 g/cc, and preferably between about 0.01 g/cc and 0.03 g/cc. The individual fibers 14 forming the fibrous nonwoven material may be selected from fibers including synthetic, nonabsorbent fibers that may or may not be wettable. Specific fiber types include, but are not limited to, polyester, nylon, co-polyester, polyethylene, polypropylene, polylactic acid, and bicomponent fibers including these materials. Of course the fibrous nonwoven material may be formed from a single nonabsorbent fiber type listed above or alternatively may be formed from a mixture of the fiber types listed above.

The surface of the nonabsorbent fibers 14 forming the fibrous material 12 may be rendered wettable by treating such fibers with a suitable surface treatment, such as a surfactant or like. The fibrous material 12 preferably further includes a binder material, such as a latex binder. The binder material is preferably present in the fibrous material 12 in an amount that corresponds to between about 20% by weight to about 60% by weight of the fibrous material 12. The individual fibers 14 forming the fibrous material preferably have a denier in the range from about 5 to about 25, preferably from about 6 to about 10. Each of the fibers 14 forming the fibrous material preferably has a fiber diameter within the range of 11 μm and 100 μm. In preferred embodiments of the invention, the fibrous material 12 is completely free of cellulosic material.

The fibrous material 12 preferably has a basis weight in the range of about 50 gsm (g/m$^2$) to about 150 gsm, preferably from about 60 gsm to about 90 gsm (including the binder material). The fibrous material 12 preferably has a thickness of between about 2 mm to about 6 mm as measured by a Ames Micrometer (Ames Waltman Mass., Model ADP1132, 175 g on the 1⅛" foot=0.384 psi). A fibrous material 12 particularly suitable for use in the present invention is a material made from a randomized web sprayed with binder from both sides of the web, having a basis weight of 86 gsm, formed from 100% 6 denier polyester fibers, having a thickness of about 3 mm, and including about 40% latex binder by weight, commercially available under product code SCN09-038 from Kem-Wove, Inc., Charlotte, N.C.

As shown in FIG. 1, the absorbent composite material 10 further includes superabsorbent polymer 22 dispersed within the fiber matrix 16. The superabsorbent polymer 22 is preferably present in the fibrous material 12 in an amount that corresponds to between about 100% to about 150% by weight of the fibrous material 12, e.g. between about 80 gsm and about 120 gsm.

For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the products offered by Sumitomo Seika Chemicals Co., Ltd. of Osaka, Japan, under the designation of SA70 and BA40B. The superabsorbent polymer 22 present in the absorbent composite 10 may consist of a single superabsorbent such as SA70 or alternatively the superabsorbent polymer 22 may consist of a mixture of superabsorbent polymers such as a mixture of SA70 and BA40B. In addition, different superabsorbent polymers may be arranged in a layered arrangement, for example the faster rate BA40B may be arranged above the SA70.

Referring again to FIG. 1, the absorbent composite material 10 further includes an absorbent mixture 24 arranged adjacent to the top surface 18 of the fibrous material 12. The absorbent mixture 24 includes superabsorbent polymer 26 and adhesive 28. Preferably the absorbent mixture 24 consists of a mixture of superabsorbent polymer 26 and adhesive 28. The mixture 24 preferably includes between about 90% and about 98% superabsorbent by weight and between 10% and about 2% adhesive by weight. Preferred superabsorbents for use in the mixture include Sumitomo SA70 and Sumitomo BA40B, commercially available from Sumitomo Seika Chemicals, Co., Ltd., Osaka, Japan. Preferably a hot melt adhesive is used as the adhesive in the mixture 24. A particularly suitable adhesive is HB Fuller NW1023 hot melt adhesive, commercially available from HB Fuller Company, St. Paul, Minn. The mixture 24 is preferably applied to the top surface 18 of the fibrous material 12 in an add on amount of between about 80 gsm and 100 gsm. This add on amount of the mixture 24 corresponds to between about 100% to 150% by weight of the fibrous material 12.

In lieu of the absorbent mixture 24 described above, a simple layer of adhesive could alternatively be applied adjacent to the top surface 18 of the fibrous material 12. In such an embodiment the adhesive would not provide additional absorbency to the composite material 10 but would rather simply help prevent the superabsorbent polymer 22 from "dusting out" of the fiber matrix 16.

Referring again to FIG. 1, the absorbent composite material 10 further includes a superabsorbent retention layer 30. As shown in FIG. 1, the superabsorbent retention layer 30 is arranged adjacent to a top surface 32 of the mixture 24 and is held in place by the mixture 24. The superabsorbent retention layer 30 functions to prevent the superabsorbent polymer 22 from "dusting out" of the fiber matrix 16.

The superabsorbent retention layer 30 may also be adapted to wick fluid in a longitudinal and transverse direction of the composite material 10 so that the composite material 10 can fully utilize its absorbent attributes.

In one embodiment of the invention, the superabsorbent retention layer 30 may consist of a wetlaid tissue having a basis weight in the range of about 10 gsm to about 20 gsm, such as a 17 gsm wetlaid tissue commercially available as Little Rapids type 2004 wetlaid tissue, Little Rapids Corp., Green Bay, Wis.

In another embodiment of the invention, the superabsorbent retention layer 30 may consist of fibrous material including wood pulp fibers, polyester fibers, rayon fibers, or combinations thereof. The superabsorbent retention layer 30 may also comprise thermoplastic fibers for the purpose of stabilizing the layer and maintaining its structural integrity. Examples of materials suitable for the superabsorbent retention layer 30 are through air bonded pulp sold by Buckeye Technologies, Inc. of Memphis, Tenn. under the designation Vizorb 3008 which has a basis weight of 100 gsm and Vizorb 3010 which has a basis weight of 90 gsm.

Another example of a material suitable for use as the superabsorbent retention layer 30 is a calendared airlaid material of the type commercially available from EAM Corporation, Jessup, Ga. under the designation Novathin. When calendared airlaid materials are used as the superabsorbent retention layer 30 such materials preferably have a basis weight in the range of about 40 gsm to about 90 gsm. The superabsorbent retention layer 30 is preferably free of superabsorbent polymer.

Another example of a materials suitable for use as the superabsorbent retention layer 30 are commercially available paper towel materials.

Figure 2:
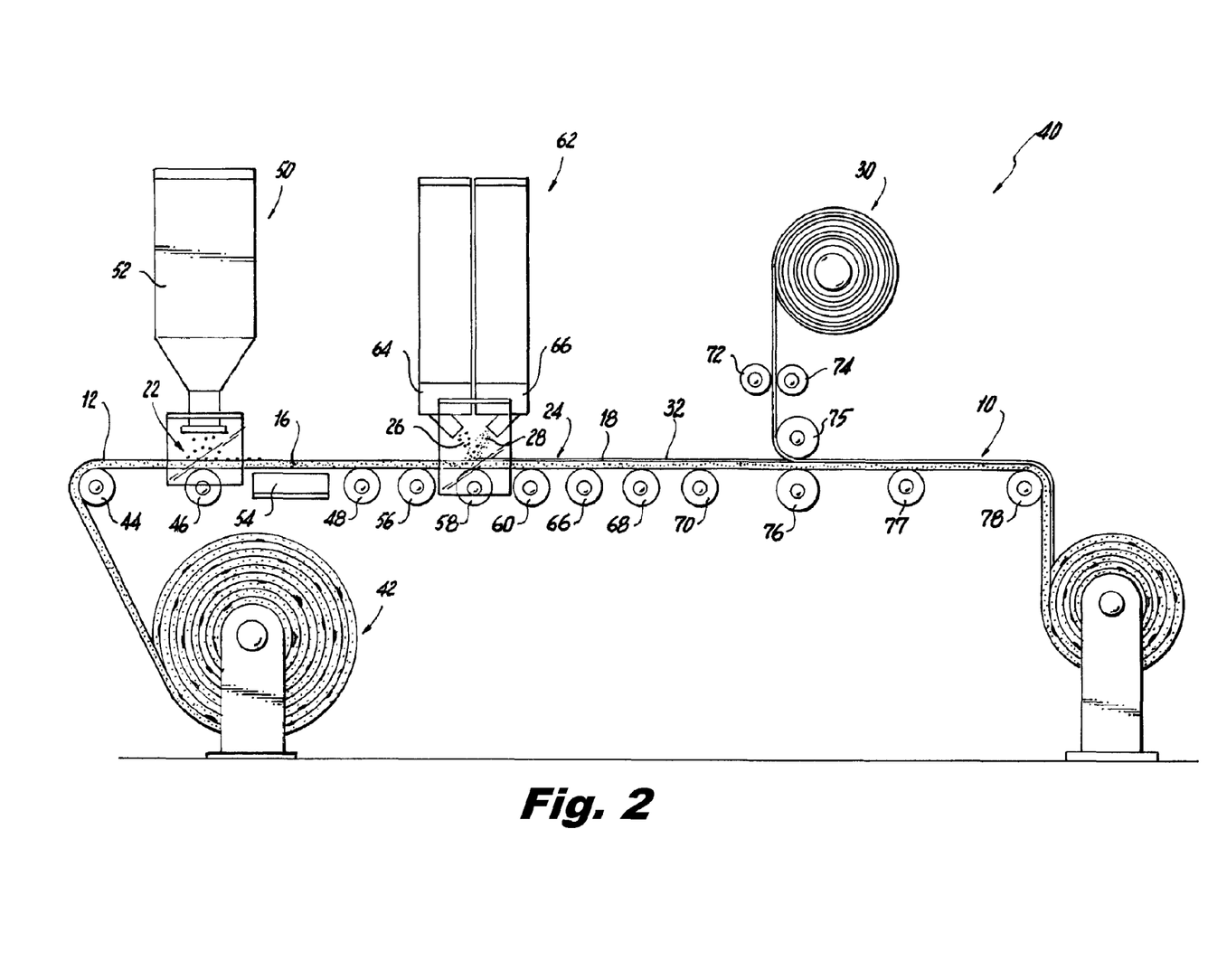
FIG. 2 is a schematic view of an apparatus for making the absorbent composite material shown in FIG. 1.

A method of making the absorbent composite material 10 will now be described with reference to FIG. 2 which depicts a schematic representation of an apparatus 40 for making the absorbent composite material 10. As shown in FIG. 2, a web of fibrous material 12 is fed from a supply roll 42 and conveyed in a machine direction by a plurality of rolls 44, 46 and 48 to a superabsorbent application station 50. The superabsorbent application station 50 comprises a metering device 52 structured and arranged to apply a selected amount of superabsorbent polymer 22 to a top surface 18 of the fibrous material 12. Metering devices for applying particulate material to a substrate are well known to those of skill in the art. Of course, any suitable means known to those of skill in the art, such as a pressure fed nozzle, brush metering roll, or the like, may be used to apply the superabsorbent polymer material 22 to the top surface 18 of the fibrous material 12. After the superabsorbent polymer material 22 is applied to the top surface 18 of the fibrous material 12, the fibrous material 12 is conveyed over a high frequency vibrator 54 that functions to mechanically force the superabsorbent polymer 22 into the fibrous matrix 16 of the fibrous material 12. Alternatively, a vacuum arranged below the bottom surface 20 of the fibrous material 12 may be used to draw the superabsorbent polymer 22 into the fibrous matrix 16.

Thereafter, the fibrous material 12 is further conveyed in a machine direction by a plurality of rolls 56, 58 and 60 to an absorbent mixture application station 62. The absorbent mixture application station 62 includes a metering device 64 for applying a stream of superabsorbent polymer 26 to the top surface 18 of the fibrous material 12. The absorbent mixture application station 62 further includes a hot melt adhesive applicator 66 which is directed at the fibrous material 12 and adapted to apply a stream of adhesive 28 to the top surface 18 of the fibrous material 12. Preferably the adhesive 28 stream and superabsorbent polymer 26 stream mix in mid air, thereby forming the absorbent mixture 24, and then the absorbent mixture 24 is deposited on the top surface 18 of the fibrous material 12.

Thereafter, the fibrous material 12 is further conveyed in a machine direction by a plurality of rolls 66, 68 and 70. The superabsorbent retention layer 30 is then arranged adjacent to the top surface 32 of the mixture 24 by means of rolls 72 and 74. Then the substrate 12 and superabsorbent retention layer 30 are passed through nip rolls 75 and 76 to thereby adhere the superabsorbent retention layer 30 to the absorbent mixture 24. Thereafter the completed absorbent composite material 10 is further conveyed in a machine direction by rolls 77 and 78 and may be arranged in a rolled form for storage or may be further conveyed for incorporation into a disposable sanitary absorbent product such as a sanitary napkin, pantiliner, tampon, diaper, adult incontinence product, or the like.

Figure 3:
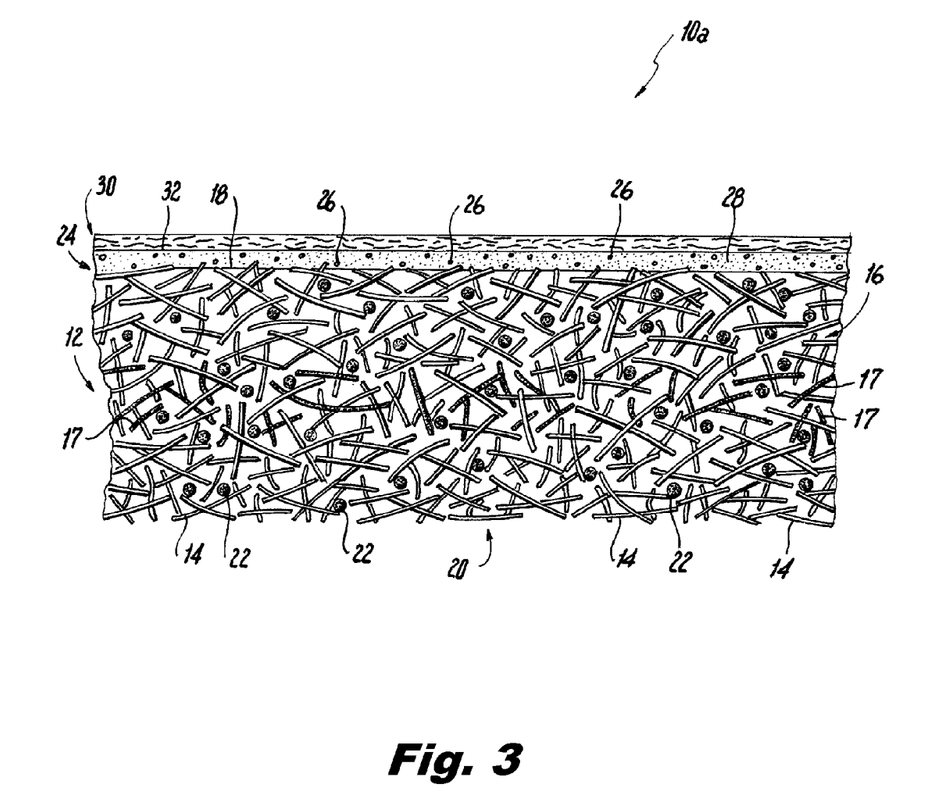
FIG. 3 is a sectional schematic view of an absorbent composite material according to a second embodiment of the present invention

Reference is made to FIG. 3 which illustrates a sectional view of an absorbent composite material 10a according to a second embodiment of the present invention. Absorbent composite material 10a includes the same features as described above with regard to composite material 10, however absorbent composite material 10a further includes a plurality of absorbent fibers 17. As shown, the absorbent fibers 17 are impregnated within the fiber matrix 16. The absorbent fibers 17 are preferably present in the fibrous material 12 in an amount between 5% to about 100% by weight of the fibrous material 12, corresponding to about 3 gsm to about 60 gsm. The absorbent fibers 17 are preferably selected from cellulosic fiber types, such as, but not limited to, hard wood pulp, soft wood pulp, rayon, and cotton. The absorbent material 10 may include a single absorbent fiber type of those listed above or in the alternative may include multiple fiber types of those listed above (i.e. a mixture of absorbent fibers). Each of the absorbent fibers 17 preferably has fiber diameter within the range of 10 µm and 40 µm. The individual fibers 14 forming the fibrous material 12 and the absorbent fibers 17 are selected such that each of the individual fibers 14 has a fiber diameter that is at least 1 lam greater than a fiber diameter of each of the absorbent fibers 17.

Figure 4:
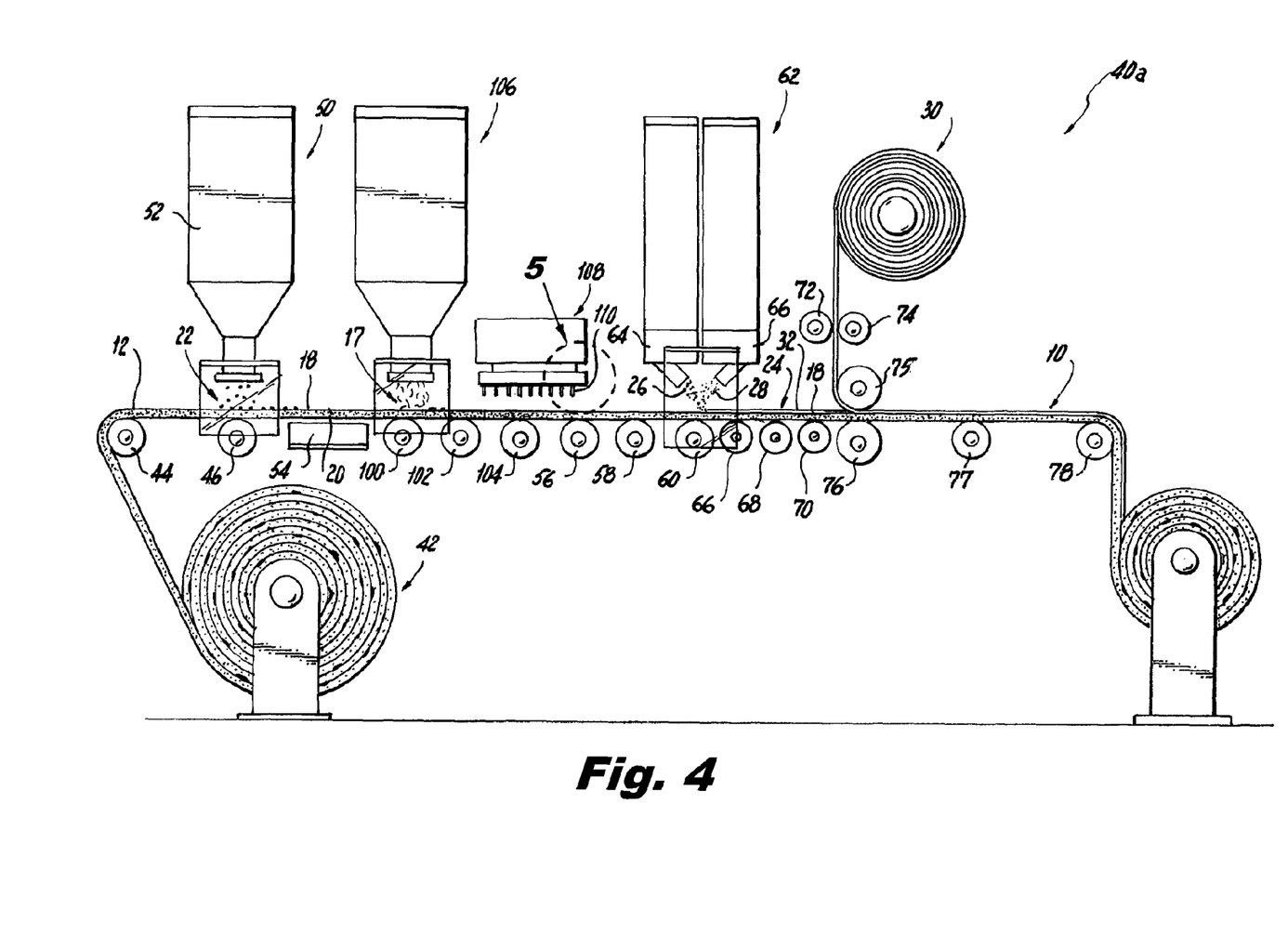
FIG. 4 is a schematic view of an apparatus for making the absorbent composite material shown in FIG. 3.

A method of making the absorbent composite material 10a will now be described with reference to FIG. 4 which depicts a schematic representation of an apparatus 40a for making the absorbent composite material 10. As shown in FIG. 4, a web of fibrous material 12 is fed from a supply roll 42 and conveyed in a machine direction by a plurality of rolls 44, 46 and 48 to a superabsorbent application station 50. The superabsorbent application station 50 comprises a metering device 52 structured and arranged to apply a selected amount of superabsorbent polymer 22 to a top surface 18 of the fibrous material 12. Metering devices for applying particulate material to a substrate are well known to those of skill in the art. Of course, any suitable means known to those of skill in the art, such as a pressure fed nozzle, brush metering roll, or the like, may be used to apply the superabsorbent polymer material 22 to the top surface 18 of the fibrous material 12. After the superabsorbent polymer material 22 is applied to the top surface 18 of the fibrous material 12, the fibrous material 12 is conveyed over a high frequency vibrator 54 that functions to mechanically force the superabsorbent polymer 22 into the fibrous matrix 16 of the fibrous material 12. Alternatively, a vacuum arranged below the bottom surface 20 of the fibrous material 12 may be used to draw the superabsorbent polymer 22 into the fibrous matrix 16.

Thereafter the fibrous material is further conveyed in a machine direction by rolls 100, 102 and 104 to a gravity fed hopper 106, or the like, that is utilized to apply a selected amount of absorbent fibers 17 to a top surface 18 of the fibrous material 12. If required, the material forming the absorbent fibers may be fed through a lickerin or a hammermill prior to the absorbent fibers being fed into the gravity fed hopper (not shown in the drawings). Thereafter, the fibrous material 12 is further conveyed in a machine direction and passed through a conventional needlepunch apparatus 108 of the type known to those of skill in the art. The needlepunch apparatus 108 functions to impregnate the absorbent fibers 17 within the fibrous material 12 by means of a plurality of needles 110.

Figure 5:
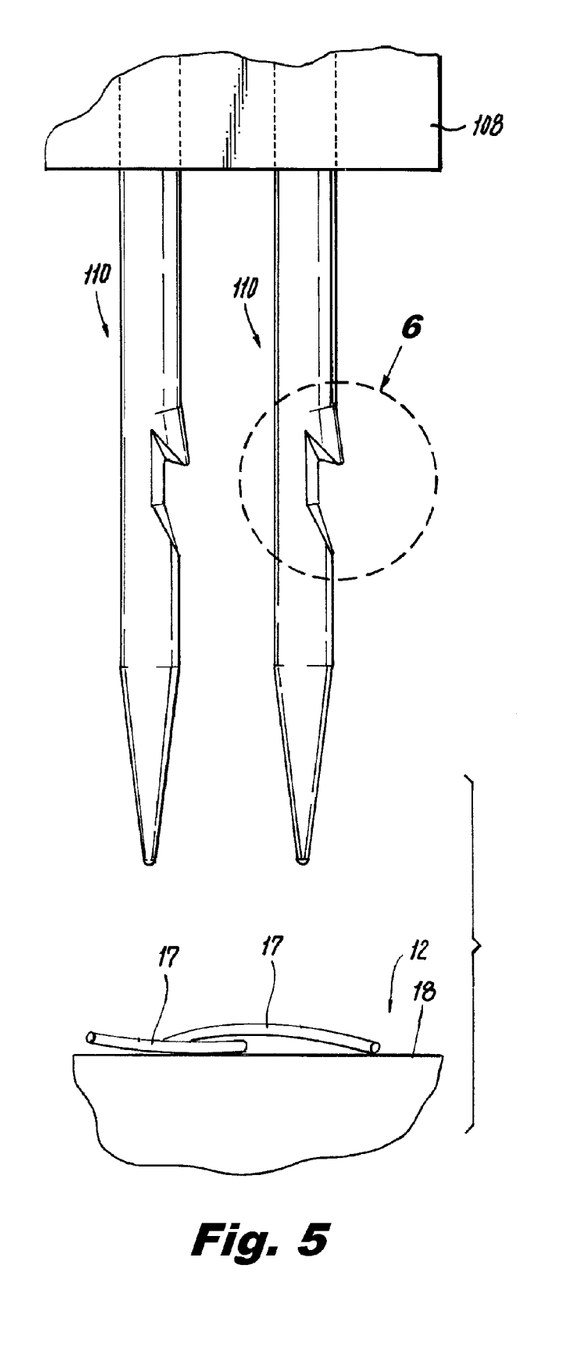
FIG. 5 is a schematic view of the encircled portion of the apparatus shown in FIG. 4 depicting a needle employed in the apparatus, a top surface of a fibrous material, and absorbent fibers arranged on the top surface of the fibrous material.
Figure 6:
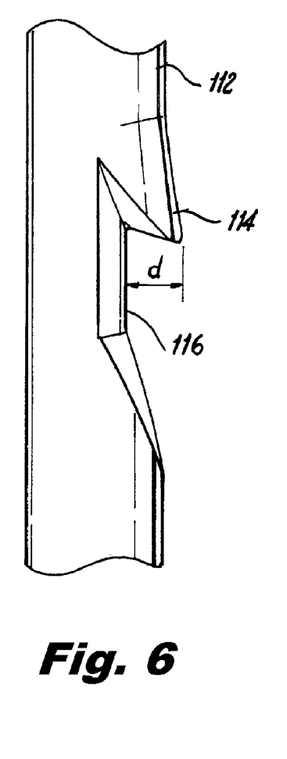
FIG. 6 is a detailed view of the encircled portion of the needle shown in FIG. 5.
Figure 7:
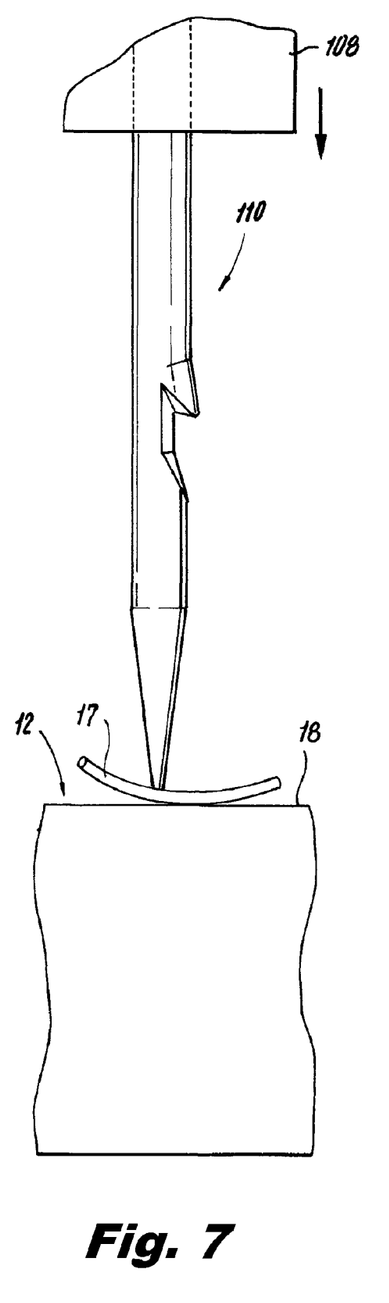
FIGS. 7-10 depict the manner in which the needle impregnates the absorbent fiber within the fibrous material.
Figure 8:
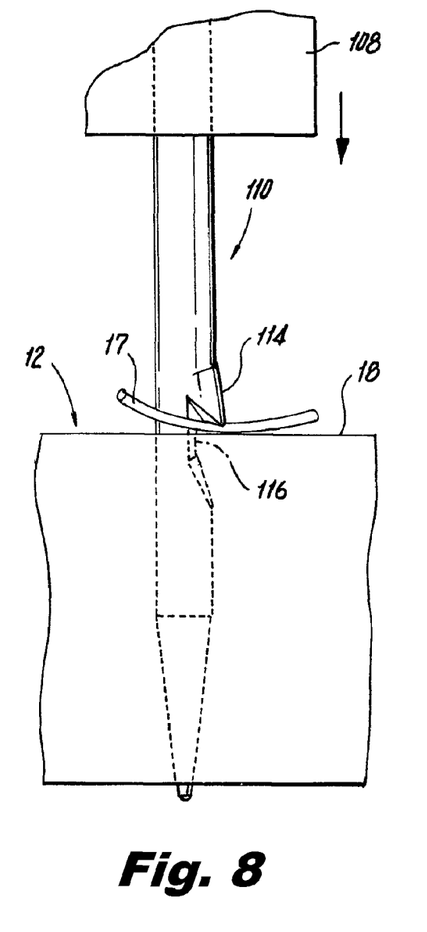
Figure 9:
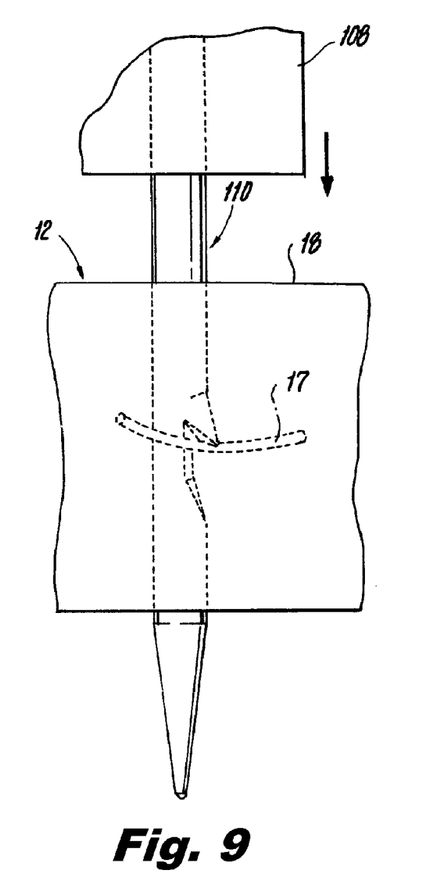
Figure 10:
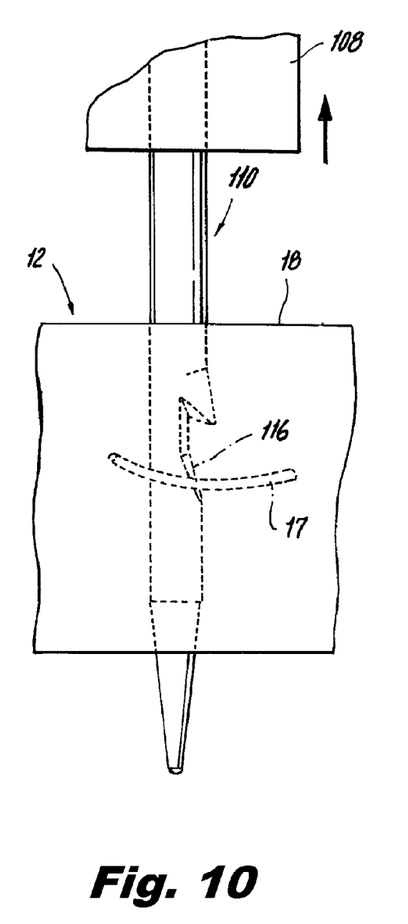

As is known to those of skill in the art, a conventional needlepunch apparatus includes a plurality of needles that are normally adapted to mechanically orient and interlock the fibers of a spunbonded or carded web. In the present invention, the needles 110 of the needlepunch apparatus 108 are used to impregnate absorbent fibers 17 within the fibrous material 12. A needle 110 suitable for use in the method described herein is depicted in FIG. 5 and FIG. 6. As shown in FIG. 6, the needle 110 generally includes a blade 112, a barb 114, and a throat section 116. The total barb depth of the barb 114 is indicated by letter "d" in the FIG. 6.

For purposes of the present invention, it is critical that the barb depth "d" is selected such that a radius of each of the absorbent fibers 17 is smaller than the barb depth "d". The radius of each absorbent fiber 17 is at least 0.5 µm smaller, for example 1 lam smaller than the barb depth. In addition the barb depth "d" should be selected such that each of the individual fibers 14 of the fibrous material 12 has a radius that is larger than the barb depth "d". The radius of each individual fiber 14 of the fibrous material 12 is at least 0.5

μm larger, for example 1 μm larger than the barb depth. If you have a multiple denier fibrous material 12, the diameter of the smallest diameter fiber 14 must be larger than the diameter of each of the absorbent fibers 17.

By selecting barb depth "d" as described above, the plurality of needles 110 in the needlepunch apparatus effectively grasp the absorbent fibers 17 and thus can impregnate such absorbent fibers 17 within the fibrous material 12, as shown in FIGS. 7-10. On the other hand, the plurality of needles 110 will not grasp the individual fibers 14 of the fibrous material 12 and thus will not destroy the "high loft" properties of the fibrous material 12. In this manner the final absorbent composite material 10 is provided with superior fluid handling properties while still retaining the high loft properties of the fibrous material 12. Needles particularly useful in the present method are commercially available from the Foster Needle Co., Inc., Manatowoc, Wis., under product designation "The Foster Formed Barb".

Thereafter, the fibrous material 12 is further conveyed in a machine direction by a plurality of rolls 56, 58 and 60 to an absorbent mixture application station 62. The absorbent mixture application station 62 includes a metering device 64 for applying a stream of superabsorbent polymer 26 to the top surface 18 of the fibrous material 12. The absorbent mixture application station 62 further includes a hot melt adhesive applicator 66 which is directed at the fibrous material 12 and adapted to apply a stream of adhesive 28 to the top surface 18 of the fibrous material 12. Preferably the adhesive 28 stream and superabsorbent polymer 26 stream mix in mid air, thereby forming the absorbent mixture 24, and then the absorbent mixture 24 is deposited on the top surface 18 of the fibrous material 12.

Referring again to FIG. 4, the fibrous material 12 is further conveyed in a machine direction by a plurality of rolls 66, 68 and 70. The superabsorbent retention layer 30 is then arranged adjacent to the top surface 32 of the mixture 24 by means of rolls 72 and 74. Then the substrate 12 and superabsorbent retention layer 30 are passed through nip rolls 75 and 76 to thereby adhere the superabsorbent retention layer 30 to the absorbent mixture 24. Thereafter the completed absorbent composite material 10 is further conveyed in a machine direction by rolls 77 and 78 and may be arranged in a rolled form for storage or may be further conveyed for incorporation into a disposable sanitary absorbent product such as a sanitary napkin, pantiliner, tampon, diaper, adult incontinence product, or the like.

Absorbent composite materials 10 according to the to the present invention, as described herein above, are thin, lofty and exhibit superior resiliency properties in both the dry and wet state. Surprisingly, absorbent composite materials 10 according to the present invention exhibit the above properties while at the same time exhibiting superior fluid handling characteristics.

Figure 11:
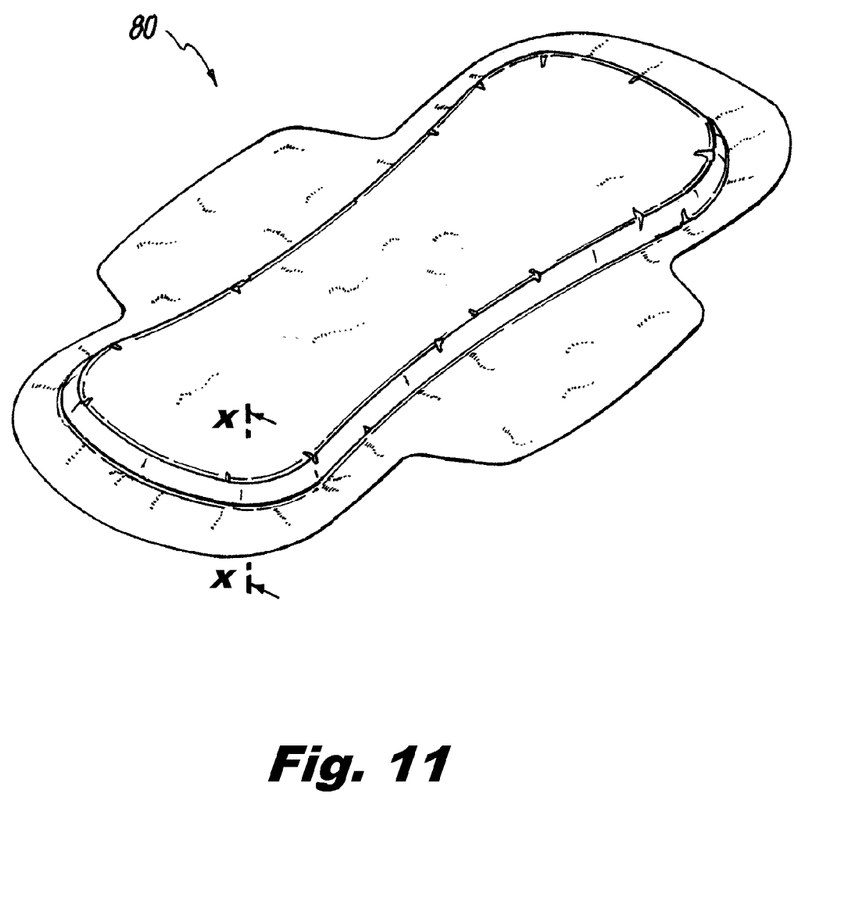
FIG. 11 is a perspective view of an absorbent article according to the present invention.
Figure 12:
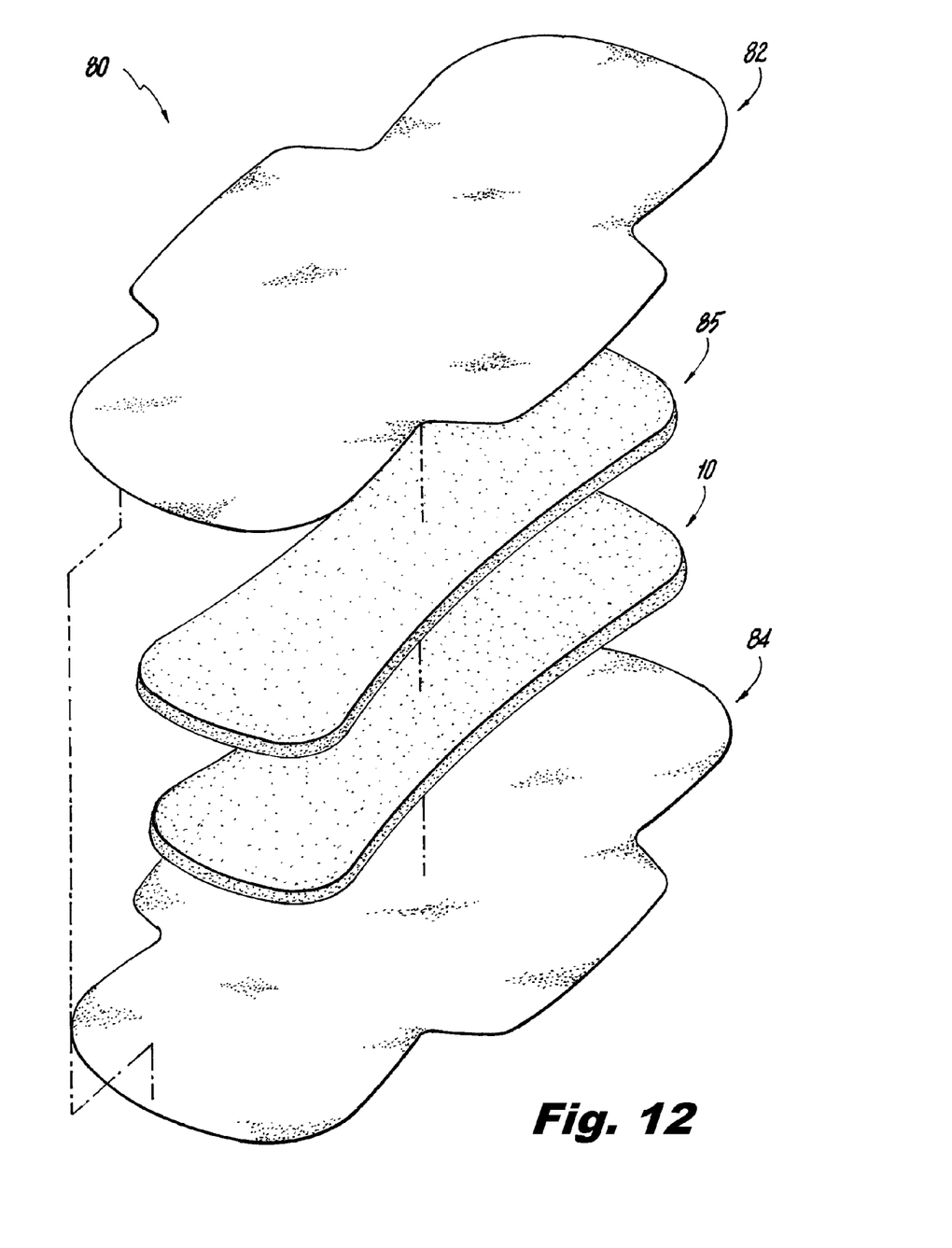
FIG. 12 is an exploded perspective view of the article shown in FIG. 11 revealing the constituent layers thereof.

Reference is made to FIGS. 11-14 which depict an absorbent article, and in particular a sanitary napkin 80, in accordance with the present invention. As shown in FIG. 12, the sanitary napkin 80 generally includes a liquid permeable cover layer 82, a liquid impermeable barrier layer 84 and the absorbent composite material 10 arranged therebetween. The sanitary napkin 80 may further optionally include a fluid distribution layer 85 arranged between the cover layer 82 and the absorbent composite material 10.

The cover layer 82 may be a relatively low density, bulky, high-loft non-woven web material. The cover layer 82 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 82 has a basis weight in the range of about 10 gsm to about 75 gsm.

Bi-component fibers may be made up of a polyester layer and a polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layer and/or to the barrier layer.

The cover layer 82 preferably has a relatively high degree of wettability, although the individual fibers comprising the cover may not be particularly hydrophilic. The cover material should also contain a great number of relatively large pores. This is because the cover layer 82 is intended to take-up body fluid rapidly and transport it away from the body and the point of deposition. Therefore, the cover layer contributes little to the time taken for the napkin to absorb a given quantity of liquid (penetration time).

Advantageously, the fibers which make up the cover layer 82 should not lose their physical properties when they are wetted, in other words they should not collapse or lose their resiliency when subjected to water or body fluid. The cover layer 82 may be treated to allow fluid to pass through it readily. The cover layer 82 also functions to transfer the fluid quickly to the underlying layers of the napkin. Thus, the cover layer 82 is advantageously wettable, hydrophilic and porous. When composed of synthetic hydrophobic fibers such as polyester or bi-component fibers, the cover layer 82 may be treated with a surfactant to impart the desired degree of wettability.

Nonwoven cover materials particularly suitable for use in the present invention are hot-through air bonded cover materials commercially available from Shalag Industries, Ltd., Upper Galilee, Israel, under product codes STA4ETW27, STA5ETW27, STAFEPW27, STA5EPW27, STAPPER22 and STAFETW22.

Alternatively, the cover layer 82 can also be made of polymer film having large pores. Because of such high porosity, the film accomplishes the function of quickly transferring body fluid to the inner layers of the underlying absorbent layers. The cover layer 82 may be attached to the underlying absorbent composite material 10 and/or the barrier layer 84, by adhesion and/or other suitable means know to those of skill in the art. The cover layer 82 may also be attached to the underlying fluid distribution layer 85 if such layer is employed.

Underlying the cover layer 82 is the optional fluid distribution layer 85. The fluid distribution layer 85 functions to receive body fluid from the cover layer 82 and hold the same until the absorbent composite 10 has an opportunity to absorb the fluid. The fluid distribution layer 85 is preferably more dense than and has a larger proportion of smaller pores than the cover layer 82. These attributes allow the fluid distribution layer 85 to contain the body fluid and hold it away from the outer side of the cover layer 82, thereby preventing fluid from rewetting the cover layer 82.

The fluid distribution layer 85 may consist of fibrous material including wood pulp fibers, polyester fibers, rayon fibers, or combinations thereof. The fluid distribution layer may also comprise thermoplastic fibers for the purpose of stabilizing the layer and maintaining its structural integrity.

Examples of materials suitable for the fluid distribution layer 85 are through air bonded pulp materials sold by Buckeye Technologies, Inc. of Memphis, Tenn. under the designation Vizorb 3008 which has a basis weight of 100 gsm and Vizorb 3010 which has a basis weight of 90 gsm.

Another example of a material suitable for use as the fluid distribution layer 85 is a calendared airlaid material of the type commercially available from EAM Corporation, Jessup, Ga. under the designation Novathin. The fluid distribution layer 85 is preferably free of superabsorbent polymer.

Underlying absorbent composite material 10 is a barrier layer 84 comprising a liquid-impervious film material so as to prevent liquid that is entrapped in the absorbent composite layer 10 from egressing the sanitary napkin and staining the wearer's undergarment. The barrier layer 84 is preferably made of polymeric film, although it may be made of liquid impervious, air-permeable material such as repellent-treated non-woven or micropore films or foams.

The barrier layer 84 may be breathable, i.e., permits vapor to transpire. Known materials for this purpose include nonwoven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 82 and the barrier layer 84 are preferably joined along their marginal portions so as to form an enclosure or flange seal that maintains the absorbent composite layer 10 captive. The joint may be made by means of adhesives, heat-bonding, ultrasonic bonding, radio frequency sealing, mechanical crimping, and the like and combinations thereof.

Positioning adhesive may be applied to a garment facing surface of the barrier layer 84 for securing the napkin 80 to a garment during use. The positioning adhesive may be covered with removable release paper so that the positioning adhesive is covered by the removable release paper prior to use.

Absorbent articles of this invention may or may not include wings, flaps or tabs for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

Figure 13:
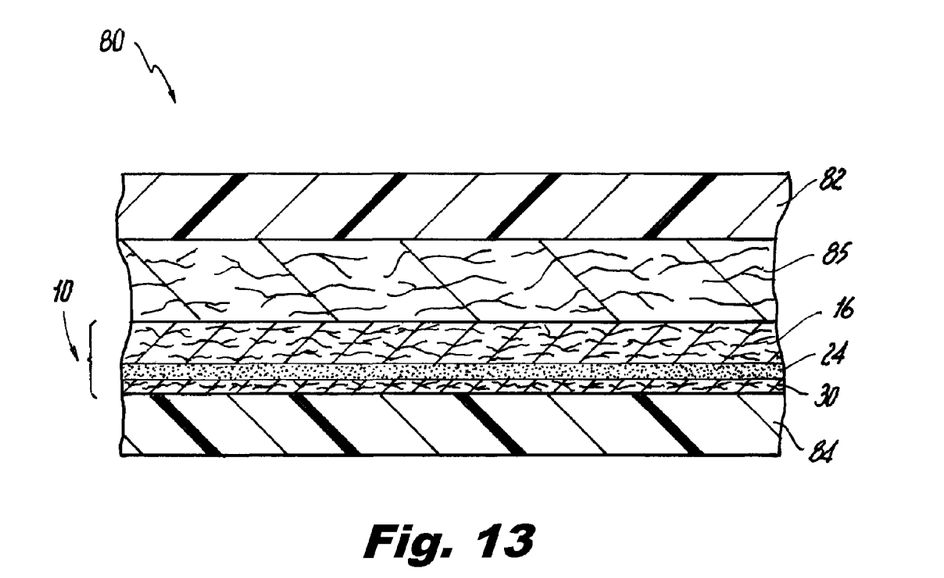
FIG. 13 is sectional view taken along line x-x in FIG. 11 showing one embodiment of the absorbent article shown in FIG. 11.

Reference is now made to FIGS. 13 and 14 which depict sectional views taken along line x-x in FIG. 11 and depict alternative embodiments of the sanitary napkin 80 shown in FIG. 11. As shown in FIG. 13, the absorbent composite material 10 may be arranged in the sanitary napkin 80 such that the superabsorbent retention layer 30 is arranged in adjacent surface to surface contact with the barrier layer 84. The embodiment of the napkin 80 shown in FIG. 13 includes a fluid distribution layer 85. Of course, however the fluid distribution layer 85 could be omitted such that the second surface 20 of the fibrous material 12 is arranged in surface to surface contact with the cover layer 82.

Figure 14:
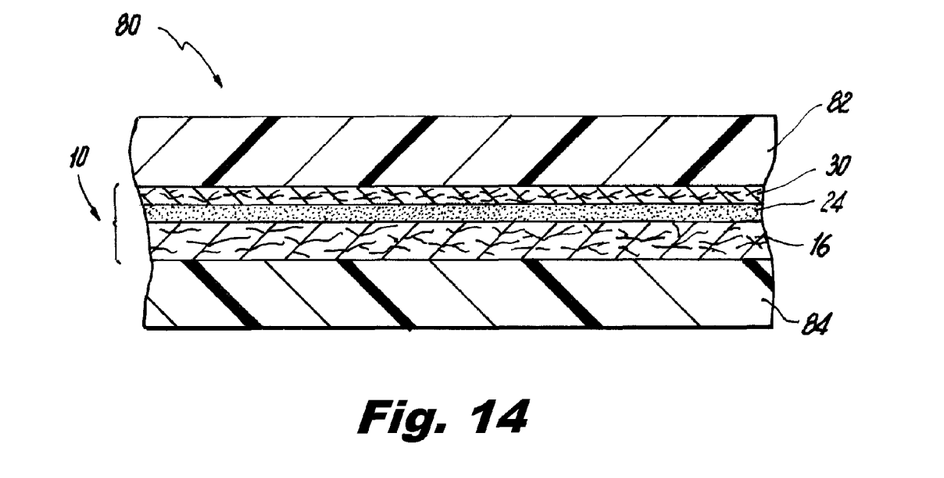
FIG. 14 is sectional view taken along line x-x in FIG. 11 showing an alternate embodiment of the absorbent article shown in FIG. 11.

Alternatively, as shown in FIG. 14, the absorbent composite material 10 may be arranged in the sanitary napkin 80 such that the superabsorbent retention layer 30 is arranged in adjacent surface to surface contact with the cover layer 82.

Absorbent articles according to the present invention, as described above, are thin, cushiony, soft, exhibit superior resiliency properties in both the dry and wet state, and also exhibit superior fluid handling characteristics.

I claim:

1. An absorbent article comprising:
    a liquid permeable cover layer;
    a liquid impermeable barrier layer; and
    an absorbent composite material arranged between the cover layer and the barrier layer; wherein the absorbent composite material comprises:
    a) a fibrous material having a density lower than 0.05 g/cc, the fibrous material including a plurality of individual fibers forming a fiber matrix and a latex binder material present in an amount from about 40% by to about 60% by weight of the fibrous material, the fibrous material having first and second opposed surfaces,
    b) superabsorbent polymer dispersed within the fiber matrix, and
    c) an absorbent mixture covering the first surface of the fibrous material, the absorbent mixture comprising between about 90% and about 98% superabsorbent polymer by weight and between about 10% and about 2% adhesive by weight, wherein the adhesive in the absorbent mixture is a hot melt adhesive.

2. The absorbent article according to claim 1, wherein the fibrous material is a high loft nonwoven material having a density between 0.01 g/cc and 0.03 g/cc.

3. The absorbent article according to claim 2, wherein each of the individual fibers is nonabsorbent.

4. The absorbent article according to claim 2, wherein each of the individual fibers are selected from the group consisting of polyester, nylon, co-polyester, polyethylene, polypropylene, polylactic acid, and bicomponent fibers including these materials.

5. The absorbent article according to claim 1, wherein each of the individual fibers has a denier in the range of from about 5 to about 25.

6. The absorbent article according to claim 1, wherein each of the individual fibers has a denier in the range of from about 6 to about 10.

7. The absorbent article according to claim 6, wherein the fibrous material is completely free of cellulosic material.

8. The absorbent article according to claim 7, wherein the fibrous material has a basis weight of between about 50 gsm and 150 gsm.

9. The absorbent article according to claim 1, wherein the superabsorbent polymer dispersed within the fiber matrix is present in the absorbent composite in an amount between about 50% to about 150% by weight of the fibrous material.

10. The absorbent article according to claim 9, wherein the superabsorbent polymer dispersed within the fiber matrix is present in an amount of from about 80 gsm to about 150 gsm.

11. The absorbent article according to claim 1, wherein the absorbent mixture consists of the superabsorbent polymer and the hot melt adhesive.

12. The absorbent article according to claim 1, wherein the absorbent composite material further comprises a superabsorbent retention layer.

13. The absorbent article according to claim 12, wherein the superabsorbent retention layer is arranged adjacent to a top surface of the absorbent mixture.

14. The absorbent article according to claim 13, wherein the superabsorbent retention layer is a tissue material.

15. The absorbent article according to claim 13, wherein the superabsorbent retention layer is a through air bonded pulp material.

16. The absorbent article according to claim 13, wherein the superabsorbent retention layer is a calendered airlaid material.

17. The absorbent article according to claim 13, wherein the absorbent composite material is arranged such that superabsorbent retention layer is arranged in surface to surface contact with the barrier layer.

18. The absorbent article according to claim 1, further comprising a fluid distribution layer arranged between the cover layer and the absorbent composite material.

19. The absorbent article according to claim 1, further comprising a plurality of absorbent fibers arranged within the fiber matrix.

20. The absorbent article according to claim 19, wherein the absorbent fibers are present in the fibrous material in an amount between about 5% and 100% by weight of the fibrous material.

* * * * *